US005815849A

United States Patent [19]

Maletich

[11] Patent Number: 5,815,849

[45] Date of Patent: Oct. 6, 1998

[54] SUNGLASS EQUIPPED FACEMASK CONSTRUCTION

[76] Inventor: Gerard Maletich, 5228 W. 139th St., Crestwood, Ill. 60445

[21] Appl. No.: 826,580

[22] Filed: Apr. 3, 1997

[51] Int. Cl.[6] ................................ A42B 1/04; A61F 9/02

[52] U.S. Cl. ........................................ 2/427; 2/205; 2/206

[58] Field of Search ............................... 2/206, 205, 202, 2/173, 4, 427, 432, 454, 9; 128/857, 858

[56] References Cited

U.S. PATENT DOCUMENTS

| | | | |
|---|---|---|---|
| 128,451 | 7/1872 | Ackerman . | |
| 603,306 | 5/1898 | Weil | 2/4 |
| 1,035,217 | 8/1912 | McQuary, Jr. | 2/427 |
| 1,251,657 | 1/1918 | Hart | 2/205 X |
| 1,395,835 | 11/1921 | Kops | 128/206.23 |
| 1,856,879 | 5/1932 | Lufkin . | |
| 2,058,989 | 10/1936 | Issac . | |
| 2,446,530 | 8/1948 | De Grazia et al. | 2/205 |
| 3,271,781 | 9/1966 | Sontag et al. | 2/202 |
| 4,176,409 | 12/1979 | Everitt | 2/202 X |

FOREIGN PATENT DOCUMENTS

| | | | |
|---|---|---|---|
| 1415794 | 9/1965 | France | 2/173 |

*Primary Examiner*—Peter Nerbun
*Attorney, Agent, or Firm*—Henderson & Sturm

[57] ABSTRACT

A sunglass equipped facemask construction 10 including an air permeable woven facemask member 20 dimensioned to closely conform to a user's head 100 and neck 101 and having a mouth opening 23 and a pair of eye openings 22 each provided with an independent sunglass lens 30 operatively engaged by inner and outer reinforcing rings connected to the facemask.

1 Claim, 1 Drawing Sheet

SUNGLASS EQUIPPED FACEMASK CONSTRUCTION

CROSS REFRENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

This invention relates to stretchable face mask constructions in general, and more particularly to a sunglass equipped stretchable face mask.

2. Description of Related Art

As can be seen by reference to the following U.S. Pat. Nos. 128,451; 1,856,879; 2,058,989; and 2,446,530, the prior art is replete with safety hoods equipped with respirator devices and having protective eyepieces. While all of these patented constructions are more than adequate for the particular purpose and function for which they have been specifically designed, they are not suitable at all for fulfilling the role envisioned for the subject matter of the present invention.

As most cold weather sports enthusiasts such as skiers, snowboarders, ice fishermen and hunters are acutely aware, the glare encountered from snow and ice on bright sunny days makes it imperative that sunglasses be worn in conjunction with warm headgear.

Unfortunately, the presence of the sunglasses is not very compatible with the vast majority of conventional headgear and usually requires that portions of the user's face will be exposed to the elements under even ideal conditions. This situation is further exacerbated when wind conditions exist because the air flow around all but wrap-around style sunglasses will cause the user's eyes to tear thereby degrading their vision.

As a consequence of the foregoing situation, there has existed a longstanding need among cold weather enthusiasts for a new type of headgear wherein sunglasses are incorporated into the headgear construction to address all of the aforementioned problems. The provision of such a construction is a stated objective of the present invention.

BRIEF SUMMARY OF THE INVENTION

Briefly stated, the subject matter of the present invention comprises a stretchable woven face mast unit having a pair of eye openings and a mouth opening. The eye openings are equipped with a sunglass unit including a pair of individual sunglass lenses that are operatively secured in the respective eye openings in the face mask unit.

As will be explained in greater detail further on in the specification, the woven nature of the face mask fabric permits air circulation around the periphery of each of the sunglass lenses to prevent the fogging of the lenses through respiration or perspiration vapors.

BRIEF DESCRIPTION OF THE SEVERAL VIEW OF THE DRAWING

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figure 1:
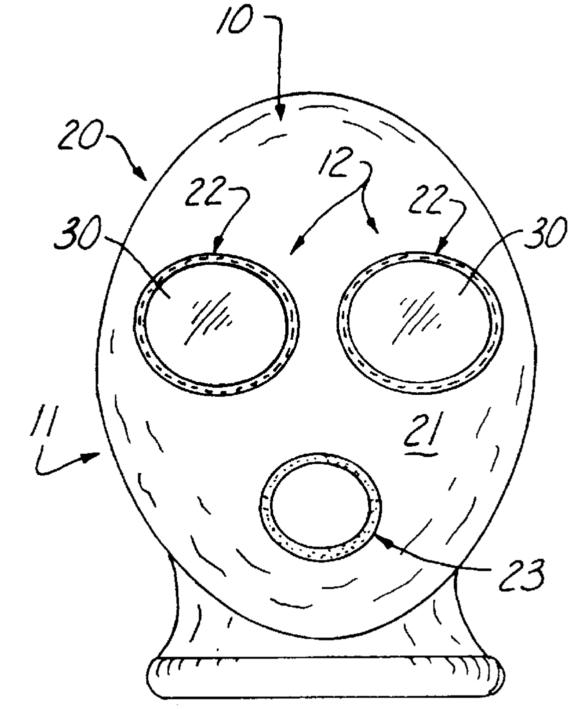
FIG. 1 is a front plan view of the sunglass equipped facemask construction that forms the basis of the present invention.

As can be seen by reference to the drawings, and in particularly to FIG. 1, the sunglass equipped facemask construction that forms the basis of the present invention is designated generally by the reference numeral 10. The facemask construction 10 comprises in general, a facemask unit 11 and a sunglass unit 12. These units will now be described in seriatim fashion.

Figure 2:
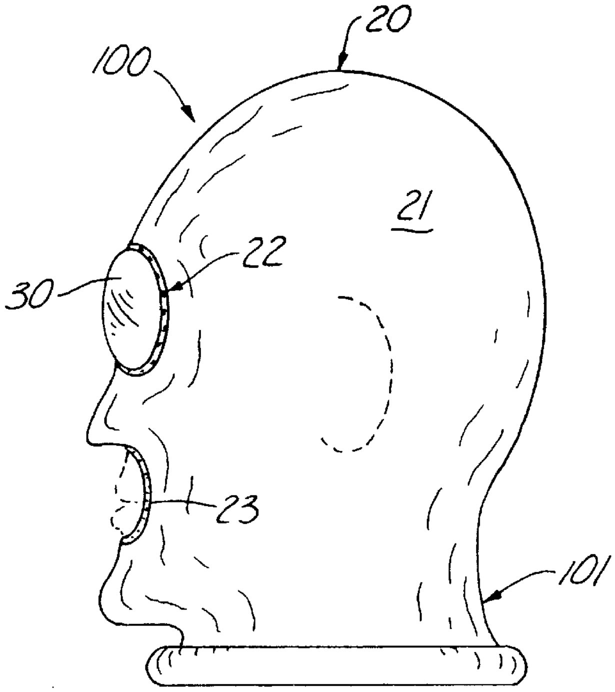
FIG. 2 is a side plan view of the facemask construction.

As can best be seen by reference to FIGS. 1 and 2, the facemask unit 11 comprises an air permeable facemask member 20 fabricated from stretchable woven material 21 such as wool, cotton, rayon or other suitable synthetic material. In addition, the facemask member 20 is provided with a pair of eye openings 22 and a single mouth opening 23. The facemask member is designed and dimensioned to cover and closely conform to the head 100 and neck 101 of the user in a well recognized fashion.

Still referring to FIGS. 1 and 2, it can be seen that the sunglass unit 12 comprises a pair of independent sunglass lenses 30 dimensioned to overlie and be respectively received within the eye openings 22 of the facemask.

Figure 3:
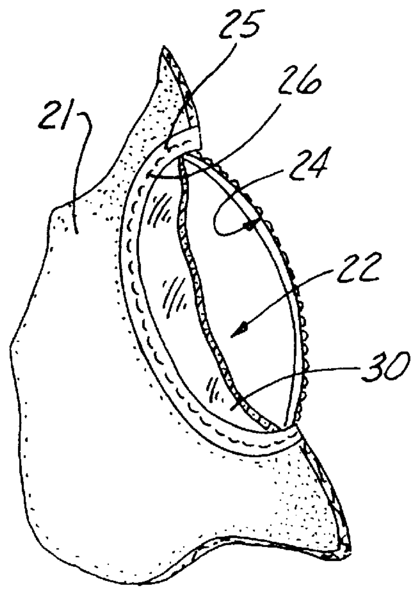
FIG. 3 is an enlarged detail view of the operative engagement between one of the sunglass lenses and one of the eye openings of the facemask; and, FIG. 4 is a cross-sectional view through one of the eye holes showing the engagement between the rings of reinforcing material and one of the sunglass lenses.
Figure 4:
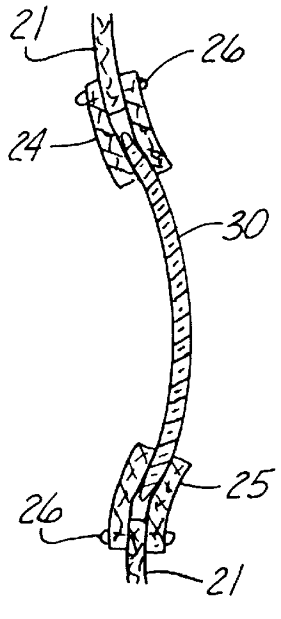

Turning now in particular to FIG. 3, it can be seen that the inner and outer periphery of each of the eye openings 22 are provided with generally circular mirror image rings of semi-rigid reinforcing material. Both the inner 24 and outer 25 ring of reinforcing material have an outer diameter greater than the diameter of both the eye opening 22 and each of the sunglass lenses and wherein both the inner 24 and outer 25 rings of reinforcing material have an inside diameter that is less than the diameter of both the eye openings 22 and the sunglass lenses 30, 30.

Still referring to FIG. 3, it can be seen that stitching 26 is provided to join both of the inner and outer rings of reinforcing material 24 and 25 to the face mask material 21 surrounding the eye openings 22 and captively engage the outer periphery of each of the sunglass lenses 30 relative to the respective eye openings 22 in a well recognized manner.

At this juncture, it should be noted that the air permeable nature of the facemask material 21 coupled with the mouth opening 23 the overall snug fit of the facemask construction 10 relative to the use's head 100 substantially minimizes the formation of vapor condensation on both the inner and outer surfaces of the lenses 30 due to the air flow passing across the interior surface of the lenses 30 by virtue of the porous nature of the face mask material 21 surrounding each of the lenses 30.

Although only an exemplary embodiment of the invention has been described in detail above, those skilled in the art will readily appreciate that many modifications are possible without materially departing from the novel teachings and advantages of this invention. Accordingly, all such modification are intended to be included within the scope of this invention as defined in the following claims.

In the claims, means-plus-function clauses are intended to cover the structures described herein as performing the recited function and not only structural equivalents, but also equivalent structures.

I claim:

1. A sunglass equipped facemask construction consisting of:

a facemask unit including a facemask member fabricated from an air permeable material and having a pair of eye openings and a single mouth opening; wherein said facemask member is stretchable and designed to closely conform to the user's head and neck; and is fabricated from a woven material selected from a class of materials that includes natural and synthetic materials; and further includes identical rings of reinforcing material associated with each of said eye openings; and a sunglass unit including a pair of independent sunglass lenses operatively disposed in said eye openings wherein said rings of reinforcing material are operatively connected on their outer periphery to said facemask member and operatively engaged adjacent their inner periphery with one of the sunglass lenses.

* * * * *